United States Patent [19]

Amon et al.

[11] Patent Number: 5,035,743
[45] Date of Patent: Jul. 30, 1991

[54] DESENSITIZING INK FOR THE PRINTING OF SELF-COPYING SHEETS

[75] Inventors: Albert Amon, Lausanne; Laszlo K. Boksanyi, La Conversion; Pierre Degott, Pully, all of Switzerland

[73] Assignee: SICPA Holding SA, Switzerland

[21] Appl. No.: 311,616

[22] Filed: Feb. 15, 1989

[30] Foreign Application Priority Data

Feb. 16, 1988 [CH] Switzerland .................. 553/88

[51] Int. Cl.$^5$ .............................................. C09D 11/00
[52] U.S. Cl. ...................................... 106/21; 503/201; 503/205; 560/157; 560/159
[58] Field of Search ................ 106/21; 503/201, 205; 560/157, 159

[56] References Cited

U.S. PATENT DOCUMENTS

| | | | |
|---|---|---|---|
| 3,105,063 | 9/1963 | Damusis | 528/77 |
| 3,658,882 | 4/1972 | Eisenman, jr. | 560/159 |
| 3,872,150 | 3/1975 | Kehr et al. | 560/33 |
| 3,916,008 | 10/1975 | Green et al. | 560/110 |
| 3,931,430 | 1/1976 | Tada et al. | 503/201 |
| 4,039,207 | 8/1977 | Ishizuka | 503/205 |
| 4,078,493 | 3/1978 | Miyamoto | 503/205 |
| 4,101,690 | 7/1978 | Miyamoto et al. | 106/21 |
| 4,337,280 | 6/1982 | Miyamoto et al. | 503/205 |
| 4,431,450 | 2/1984 | Hasegawa et al. | 106/21 |
| 4,599,111 | 7/1986 | Amon et al. | 106/21 |
| 4,725,315 | 2/1988 | Sano et al. | 106/21 |

FOREIGN PATENT DOCUMENTS

761107 11/1956 United Kingdom .

*Primary Examiner*—William R. Dixon, Jr.
*Assistant Examiner*—Helene Klemanski
*Attorney, Agent, or Firm*—Ostrolenk, Faber, Gerb & Soffen

[57] ABSTRACT

New nucleophilic urethanes are described and claimed, which are the reaction product of a monoisocyanate, a diisocyanate or a polyisocyanate with a basic alkoxylated amine whose hydroxyl functionality has been adjusted to a value of 0.5 to 2 by etherification, esterification and/or reaction with a monoisocyanate. These compounds are particularly used, individually or as a mixture, as neutralizing nucleophilic compositions in desensitizing inks for the printing by dry or humid offset, typographic, or flexographic methods, destined to locally neutralize the electrophilic layer of a chemical pressure sensitive copying set. The disclosed compounds have a better neutralizing power which allows to reduce the weight per surface unit of the desensitizing printing by at least a third.

20 Claims, No Drawings

DESENSITIZING INK FOR THE PRINTING OF SELF-COPYING SHEETS

FIELD OF THE INVENTION

The present invention relates to desensitizing inks for the printing of pressure sensitive copying sheets, shortly designed as self-copying sheets. It further relates to a new class of chemical compounds and a method for their preparation.

PRIOR ART AND TECHNICAL BACKGROUND

Self-copying sheets comprise at least two superimposed sheets whose contacting faces are coated with a layer each. Usually, the top sheet comprises on its back surface a layer of microcapsules which contain electron-donating or nucleophilic colorless or pale colored leuco dyestuffs, and a bottom sheet with a coated upper surface layer containing electron accepting or electrophilic developers. Multicopying stacks are formed by alternating these layers, i.e. the aforementioned bottom sheet has on its back surface another nucleophilic layer, and so on. The said microcapsules are locally destroyed under the action of a pressure, typically a letter of a typewriter or the stylo of a pen, and a color forming reaction takes place between the nucleophilic leuco dyestuff and the electrophilic acceptor on the upper side of the second sheet. A reproduction of the writing on the upper sheet is thus obtained on the upper surface of the lower sheet.

In some cases, there may be area portions on the second sheet where no reproduction, and thus no color formation, should appear on the second sheet or copy. Since there is no means to avoid the destruction of the microcapsules under pressure, the said areas should be neutralized on the surface of the second sheet. This is generally accomplished by a locally confined printing with a nucleophilic desensitizing ink.

The most appropriate printing methods for the application of such desensitizing inks to the copying paper are the dry offset, the wet offset or lithographic, the flexographic, and the typographic methods.

The dry offset method uses an elastomer plate having elevated active printing surfaces which are inked. The ink on the inked surface portions is transferred to a rubber cloth which will then deposit the ink on the sheet to be printed. This method requires only a low pressure for the transfer of the ink to the upper surface of a sheet having a back microcapsule coating (CFB). Thus, there is only little risk to destroy said microcapsules.

The wet offset or lithographic printing method employs a metal plate where the areas to be printed are oleophilic, and the areas not to be printed have a hydrophilic character. The oleophilic areas are inked from an ink trough followed by an inking train, whereas humidifying rollers wet the hydrophilic areas from a wetting water trough. The ink on the oleophilic areas of the plate is then transferred to a rubber cloth and further deposited on the surface to be printed.

A balance between the ink feed and the water feed must be reached on the plate in addition to the possible emulsion balance of the water within the ink. These balances are responsible for the printing sharpness, and they are in physicochemical relation with the hydrophilic-lipophilic balance (HLB).

The flexographic method uses relief surfaces formed by elastic clichés of rubber or resilient synthetic materials fixed to a printing roller. In a similar manner, the typographic method employs a matrix having elevated surface portions. The elevated portions of the two printing systems will be inked and then transmit the ink on the substrate to be printed.

The printing methods mentioned above are well known to the one skilled in the art until the least detail, and they will thus not be repeated here.

The known desensitizing inks, also named neutralizing inks, are designed to be printed by offset on certain predetermined surface areas of the accepting sheet of a chemical copying set where the sheet or the sheets already comprise at least one electrophilic accepting layer on the upper surface. It will be necessary that the desensitizing ink has a nucleophilic character to be able to neutralize the electrophilic effect of the accepting composition.

Numerous organic compounds have already been suggested and used as active nucleophilic components of desensitizing inks which are capable of neutralizing the electrophilic components of the accepting layer on predetermined surface areas in order to prevent a color formation under the effect of a pressure which destroys the microcapsules containing the nucleophilic leuco dyestuff. These nucleophilic active components are selected according to the particular printing method and the composition of the printing ink. The choice is limited since the active compound must fulfill a plurality of conditions well known to the man of the art.

Generally, the nucleophilic property of the active component is based on the presence of free electron pairs attached to electronegative atoms, especially oxygen and nitrogen, capable of combining with a pair of electron holes of an electropositive atom such as carbon, sulfur, boron, etc. Polyalkylene glycols, glycerol, long-chain fatty quaternary ammonium salts and long-chain amines have already been proposed as active nucleophilic components of desensitizing inks. These desensitizing compounds, however, have a number of inconvenients. For example, the desensitizing effect may decline under the influence of heat, humidity or light. Other compounds have a tendency to migrate on those areas of the accepting layer where a coloration should occur. Most known compounds undergo a browning after a certain time. The amines and their simple derivatives have generally a strong and disagreeable smell; some of them are toxic or allergenic.

It has been tried to overcome these drawbacks in proposing other active nucleophilic compounds. For example, the published European patent application no. 0 088 466 discloses a nucleophilic active compound which is an alkoxylated derivative of an organic compound having an active hydrogen atom such as alcohol, phenol, fatty acid, or amine, polyalkoxylated with ethylene oxide and/or propylene oxide. The German Patent DE-C3-25 26 592 describes polyalkoxylated amines which are at least partially esterified or etherified on the terminal hydroxyl groups stemming from the alkoxylation of mono and polyamines.

However, although the neutralizing compounds of the German patent DE-C3-25 26 592 bring about an improvement as to the odor and to the hydrophobicity of these compounds, it has been found that the neutralizing or desensitizing power of these compounds is comparable or even weaker than that of known compounds or to compounds which are sold as components of desensitizing inks. This fact renders the deposit of a high amount of ink necessary to obtain a perfect desensitizing effect.

However, the use of desensitizing inks has disadvantages by itself. Firstly, the drying of an ink is the longer the more the printing is thick, and the drying time is an exponential function and not a linear function of the thickness. This fact is of the highest importance since, if the drying speed is too slow, an off-set of the printed sheets which are deposited in stacks at the end of the printing machine is observed, or the off-set of successive layers when the paper is wound on rolls.

Secondly, and from an economical viewpoint, the total cost of a desensitizing printing depends before all on the price of the ink, and desensitizing inks are very expensive.

SUMMARY OF THE INVENTION

There is therefore an urgent need for desensitizing inks which have an increased neutralizing power, in order to reduce the amount of the ink to be printed per unit of surface area necessary for a complete neutralization of the underlying electrophilic accepting layer and to guarantee a rapid drying.

Therefore, it is a first and major object of this invention to develop a new class of compounds which can be used as an active nucleophilic component capable of neutralizing electrophilic components and, incorporated into an ink for offset, typographic or flexographic printing, of desensitizing an electrophilic layer of a chemical copying set, whereby these compounds distinguish from known compounds by a higher neutralizing power, but still have the same advantages or necessary properties of known compounds. In regard of the generally high price of desensitizing compounds, an increase in neutralizing power of 25% would already be a great advantage and would consequently allow to reduce the thickness of the printing and the drying time.

Another object of this invention is to develop new desensitizing inks for offset, typographic and flexographic printing with the new nucleophilic compounds.

A new class of compounds has now been found which can be used advantageously as active neutralizing components in desensitizing inks for humid or dry offset, typographic or flexographic printing which are derived from ethoxylated and/or propoxylated amino compounds.

DETAILED DESCRIPTION OF THE INVENTION

The new neutralizing compounds of this invention are addition products of mono, di or polyisocyanates with ethoxylated and/or propoxylated amines, diamines, polyamines; or mono, di or trialkanolamines whose hydroxyl number has been reduced, as far as necessary or appropriate, after said alkoxylation by ether, ester or urethane formation.

The basic amino compound may be selected from the following:
ammonia
primary monoamines, primary diamines and primary polyamines (such as polyethylene imine)
secondary monoamines, diamines and polyamines
primary, secondary or tertiary alkanolamines,
but preferably the amino compound is selected from primary and secondary mono and diamines.

These amino compounds can be ethoxylated and/or propoxylated by methods known per se by the addition of amino and/or hydroxyl groups to the oxirane function of ethylene oxide and/or propylene oxide. The ethoxylation and/or the propoxylation may proceed further by the addition of hydroxyl groups generated on the opening of oxirane cycles to other excess oxirane groups, the final alkoxy group content of the amino compound being determined by the ponderal ratio between the amino compound and the oxirane compound. The hydroxyl functionality of the compound defined as the number of terminal hydroxyl groups per molecule of the intermediate, is equal to the number of active hydrogen atoms of the basic amino compound; it varies between 1 for an ethoxylated secondary amine and 4, for example for an ethoxylated primary diamine, if the amino compounds are selected from ammonia, primary or secondary monoamines and diamines, primary, secondary and tertiary alkanolamines, and the hydroxyl number may even be greater when primary and secondary polyamines are concerned.

The alkoxylated compounds, individually or mixed, are then reacted with mono, di or polyisocyanates.

The addition of a monofunctional isocyanate may be operated independently of a hydroxyl functionality of the alkoxylated compound or the average functionality of a mixture of alkoxylated compounds.

In the case of the reaction with an isocyanate having a functionality equal to or greater than 2, e.g. diisocyanate or polyisocyanate, care must be taken that the average hydroxyl functionality of the alkoxylated product or mixture be smaller than 2 or preferably near 1. Otherwise, it will be difficult to control the final viscosity of the product or even to avoid gelification, or the amount of di or polyisocyanate to be added is too low for the urethane formation to bring about the desired advantages.

Therefore, it will be necessary to reduce the average hydroxyl functionality of the alkoxylated intermediates before urethane formation. One could mix alkoxylated products having a different hydroxyl functionality in such a manner that the mixture has an average hydroxyl functionality less than 2 when alkoxylated products having a hydroxyl functionality less than 2 are introduced into the mixture and serve thus as a chain terminating agent for the polyaddition with di or polyisocyanates.

Another alternative is to reduce the hydroxyl functionality of an alkoxylated amino compound by reaction of part or the total of the hydroxy groups with a reactive monovalent group until the average hydroxyl functionality of the molecule thus obtained is lower than 2, preferably near to 1.

Possible chemical reactions are ether formation, ester formation and urethane formation. Monovalent compounds which may be used are alkyl or cycloalkyl halides, sulfonic or carboxylic acids and their reactive derivatives, and monoisocyanates.

It is possible to successively use the reactions cited above for this invention, e.g. to etherify the alkoxylated amino compounds to a certain degree, then to esterify them until the desired hydroxyl functionality is obtained. Care must be taken to avoid side reactions, e.g. between an esterification agent not fully reacted with a monoisocyanate, but this matter is well known to those skilled in the art.

It is further possible to mix alkoxylated amino compounds reacted as above, or to mix these product with non-reacted alkoxylated amino compounds in order to obtain the desired average hydroxyl functionality before the final treatment with a di or polysocyanate. The new neutralizing compounds of this invention are therefore addition compounds of mono, di or polyisocyanates with a hydroxylated compound or a mixture of hydroxylated compounds having the general structure:

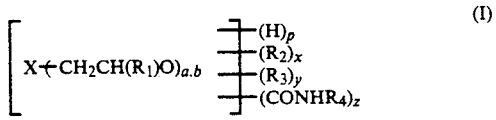

wherein the substituents H, $R_2$, $R_3$ and $CONHR_4$ are linked to oxygen atoms, and wherein:

X is the residue of the basic amino compound bonded to the $-CH_2CH(R_1)O$ groups via nitrogen or oxygen atoms, selected from ammonia, primary and secondary mono, di and polyamines, primary, secondary and tertiary alkanolamines, preferably from a diamine having the formula $H_2N(CH_2)_iNH_2$ wherein i is a number from 1 to 12, $R_1$ is independently a hydrogen atom or a methyl group, $R_2$ is an alkyl or cycloalkyl radical, preferably lower alkyl having from 1 to 4 carbon atoms such as methyl or butyl, $R_3$ is the acyl residue of a sulfonic or carboxylic acid, acyl inferior having from 2 to 5 carbon atoms such as optionally substituted acetyl, propionyl, or butyryl being preferred, or otherwise fatty acid acyl groups such as lauric ($C_{12}$), myristic ($C_{14}$), palmitic ($C_{16}$), stearic ($C_{18}$), arachidic ($C_{20}$) and behenic ($C_{22}$) being preferred, or optionally substituted benzoyl, $R_4$ is a monovalent organic group, preferably an aliphatic, cycloaliphatic or aromatic group, a is the number of alkoxy chains bonded to the basic amino compound or, in other words, the number of still active hydroxy hydrogen of the basic compound, b is the number of alkoxy groups per alkoxy chain, b being comprised between 1 and 6, x is the average of ether bound alkyl groups per molecule, x being zero or a positive number, y is the average of ester boud acyl groups per molecule, y being zero or a positive number, z is the average of urethane groups per molecule, z being zero or a positive number, and p is the number of active hydroxyl hydrogen atoms per molecule, p being equal to a $-(x+y+z)$, x, y, and z being further selected in function of a such that p is at least 0.5, preferably between 1 and 3, particularly about 1.

It is preferred that the average hydroxyl functionality p of the alkoxylated amino compounds of formula (I) or of a mixture of these compounds is comprised between 0.5 and 2 before the final isocyanate reaction.

The mono, di and polyisocyanates which are used for the final urethane reaction are commercial products. According to a preferred embodiment of this invention, a diisocyanate having the structure OCN—R—NCO wherein R is an aliphatic or cycloaliphatic divalent radical, such as hexamethylene, or an aromatic one, such as phenylene, toluylene or naphtylene, is particularly preferred.

The amount of isocyanate equivalents used in the urethane formation reaction is near to the amount of hydroxyl equivalents in the product of formula (I), preferably somewhat less, so that there is formation of one urethane group for each free hydroxyl group, or slightly less. The final hydroxyl number of the urethane product, expressed in mg KOH per g of product, is generally lower than 60, preferably lower than 20.

An important class of new neutralizing compounds of this invention has the following general structure:

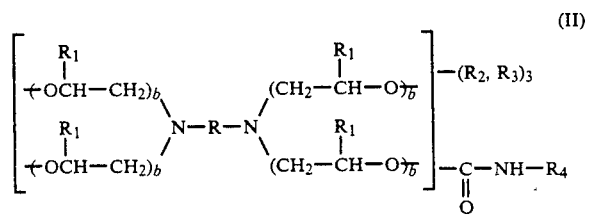

wherein:

R is a bivalent aliphatic or aromatic radical, $R_1$ is hydrogen or a methyl group, $R_2$ is is an alkyl group, preferably lower alkyl, $R_3$ is the acyl radical of a carboxylic acid having up to 22 atoms, $R_4$ is an organic group which may carry at least one substituent of the formula

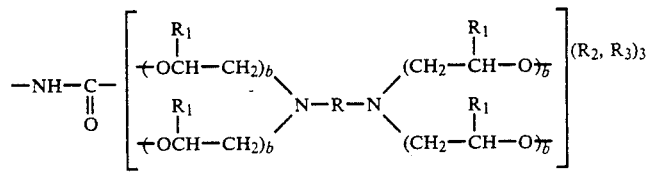

and b is a number in the range of 1 to 6.

In general formula (II), R is preferably a group of the formula $-(CH_2)_i-$ wherein i is a number from 2 to 12; the moiety $>N-R-N<$ is therefore the tetravalent radical of ethylene diamine, propylene diamine, butylene diamine, pentylene diamine, hexylene diamine up to dodecylene diamine. R may also represent a bivalent aromatic group such as phenylene, toluylene and naphtylene.

The symbols $R_1$ independently represent hydrogen or a methyl group. Details will be given below.

$R_2$ is preferably a lower alkyl group having from 1 to 4 carbon atoms. Methyl and butyl are particularly preferred.

$R_2$ may also represent the acyl radical of a carboxylic acid having up to 22 carbon atoms. The lower acyl groups such as acetyl, propionyl, butyryl and their substituted derivatives are preferred when merely three hydroxyl groups should be blocked. On the other hand, fatty acyl groups are preferred such as the acyl groups of lauric acid ($C_{12}$), myristic acid ($C_{14}$), palmitic acid ($C_{16}$), stearic acid ($C_{18}$), arachidic acid ($C_{20}$), and behenic acid ($C_{22}$) and their simple derivatives when it is intended to enhance the solubility of the final products of formula (I) in oils, thus their hydrophobicity.

If substituted acyl radicals are used, care must be taken that the substituents do not interfere with the following urethane formation reaction. For example, the hydroxy substituent is to be avoided, whereas the halogenes or the methoxy are acceptable.

The compounds of this invention may be prepared in several steps by methods and processes known per se.

The first step is the alkoxylation of the basic amino compound. Known methods are used. For example, the amine may be mixed with ethylene oxide and/or propylene oxide, optionally with the addition of a solvent but under anhydrous conditions, and the mixture is heated. It is also possible to add ethylene oxide and/or propylene oxide, under normal or elevated pressure, at an elevated temperature to the amine in the optional presence of a solvent under anhydrous conditions. A catalyst such as an acid or a base may be added. The molar amounts of ethylene oxide or propylene oxide which add to the amine are determined by the amounts of ethylene oxide and/or propylene oxide used. The amounts are selected such that the molecular mass of the addtion product thus obtained will have a value between about 100 and 10 000 grams per mol, preferably between about 200 and 2000, more preferably between 800 and 2000.

The addition product has the formula $$[X(CH_2CH(R_1)O)_{a \cdot b}]H_a \qquad (III)$$

wherein X, $R_1$, a and b have the meanings defined above.

In this formula (III), $R_1$ is hydrogen if ethylene oxide has been used exclusively, or $R_1$ is methyl when propylene oxide has been used. If a mixture of ethylene and propylene oxides has been employed, $R_1$ is hydrogen or methyl according to the molar ratio of the two epoxides used.

The second step of the preparation process comprises etherification, esterification or urethane formation with a monovalent compound reactive with hydroxyl groups, and these reactions in principle aim at reducing the average hydroxyl functionality of the compounds of formula (III). This step may be omitted if the alkoxylated amino compound or the mixture of these compounds has an average hydroxyl functionality less than about 2. Etherification is effected with reagents introducing a lower alkyl group such as methyl, ethyl, propyl, i-propyl, butyl, i-butyl or tert-butyl. The known etherification methods are used in this step. For example, the product of formula (II) which must not necessarily be isolated from the alkoxylation reactional mixture, is reacted with an alkyl halide having the formula $R_2$—Y where $R_2$ has the above-defined meaning and Y is an iodine, bromine or chlorine atom, or with another analogous compound where Y is a leaving group such as sulfate or tosyl. R=butyl and Y=bromine are preferred. The reaction is generally carried out at an elevated temperature, in the absence of water, in the presence of a solvent, and after having reacted the product of formula (II) with an alkali metal such as sodium or potassium.

The esterification is also a method known per se. The reagents which may be used are carboxylic or sulfonic acids and their reactive derivatives such as halides, anhydrides nad some of their esters. The reaction conditions may be varied according to the type of acylating agent used. In general, a base is used together with acyl halides whereas a tin salt or a strong acid are effective catalysts when esterification is made with the free acid. In this case, the water which is forming during the reaction must continuously be removed.

Urethane formation with monoisocyanate is also a method known per se. Details of this method are given below.

The three cited techniques can be used individually or successively in any order whatsoever, but etherification is preferred as the first step. This reaction effectively asks for very long reaction times whereas certain reactive derivatives of carboxylic or sulfonic acids, such as their halides, and the monoisocyanates are very reactive compounds with hydroxyl groups. For economical reasons, one prefers to etherify a part only of the free hydroxyl groups until x is equal to about a/2 or a/3, where x and a have the meaning already given above, and to bring afterwards the etherified product to the desired average hydroxyl functionality by esterification or urethane formation with the reactive derivative of a carboxylic or a sulfonic acid or a monoisocyanate.

The reaction product of this second step may be prepared according to the German patent specification DE-C3-25 26 592. This patent discloses the preparation of neutralizing compounds for desensitizing inks which are obtained (1) by the addition of ethylene oxide and/or propylene oxide to ammonia, alkyl amines, alkylene amines, alkenyl amines, aryl amines or cycloamines until the exhaustion of active hydrogen, and (2) etherification of at least 25%, preferably 50% or more of terminal hydroxy groups by reaction with an alkyl halide.

Although an average hydroxyl functionality of about 1, preferred by this invention, has not been disclosed in this prior art, the method of preparation given therein may also be applied here.

The starting compounds of the process according to this invention have the general structure

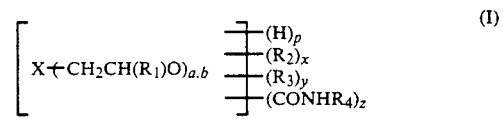

wherein X, $R_1$, $R_2$, $R_3$, $R_4$, a, b, x, y, z and p have the meanings given above.

The reaction product of this second step is therefore an ether, an ester or a monourethane having an average hydroxyl functionality of less than 2 and preferably about 1. These three functionalities can be present individually or in combination. This will say that the major part of the molecules will carry one or two free hydroxyl groups, but this doesn't exclude that a minor fraction of these molecules has no free hydroxy group at all or has three or more such groups.

For the purpose of the invention, it is not necessary to separate the mixture in order to isolate the fraction having exactly the desired hydroxyl functionality.

The process of this invention then comprises the urethane formation with the product obtained in this second step, of a mixture of these products, of the products obtained in the first step, of a mixture of such products, or of a mixture of products obtained in the first and the second step, the important point being to take care that the average hydroxyl functionality of these products or mixtures is higher than about 0.5 and generally lower than about 2, in order to introduce a sufficient amount of isocyanates and to obtain the desired advantages, whereby gelification is to be avoided and the molecular weight and the viscosity of the final product is to be controlled.

The urethane reaction is effected using a mono, di or polyisocyanate or a mixture of these compounds, preferably a diisocyanate, in a molar ratio of isocyanate to hydroxyl of about 1, preferably slightly lower, typically 0.9:1.

The hydroxyl number of the final product should be lower than about 60 mg KOH/g, values of less than 20 mg KOH/g being preferred.

The urethane reaction is operated at a medium temperature generally comprised between about 60 and about 150° C., with or without a new addition of catalyst, tertiary amines which are present in the mixture being good urethane formation catalysts.

The reaction may conducted in the absence of a solvent thus avoiding the isolation of the product. However, since urethane formation from isocyanates is an exothermic reaction, an inert solvent such as the hydrocarbons should be used to diffuse the reaction heat. An increase of temperature may also be controlled by the addition speed of the isocyanate. Finally, the urethane product is isolated from the reaction mixture and purified if necessary.

The new product of this invention is a liquid at room temperature, has a medium viscosity, is substantially colorless and odorless and is chemically stable. The product is not toxic when it is free of residual isocyanate

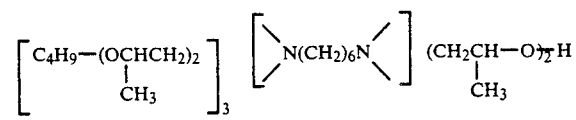

(formula I; $X = >N(CH_2)_6N<$; $R_1=CH_3$; $R_2=$n-butyl; $a=4$; $b=2$; $x=3$; $y=z=0$), obtained according to the operations described below, are placed. The product is substantially colorless and has a hydroxyl number of 79, expressed as usual in mg KOH/g.

The contents of the vessel are heated to 80° C., and 10 parts by weight of toluene diisocyanate (TDI), isomer mixture, are introduced dropwise under stirring. TDI is a commercial product.

After one hour, the addition of TDI is finished. The temperature raises at the beginning of the introduction to 95° C. and is maintained at 120° C. during the reaction time. The indicated amounts of reagents are selected to establish an equivalent ratio OH/NCO of 1.1 corresponding to a molar ratio hydroxyether/diisocyanate of 2.1:1.

After cooling, a nearly colorless liquid is obtained having a weight average molecular mass of $2600\pm200$, an average number molecular mass of $1100\pm80$, a viscosity of 2.5 Pa.s at 25° C., a nitrogen content of $5.2\pm0.1\%$ and a hydroxyl number of about 19 mg KOH/g.

The final product has the formula

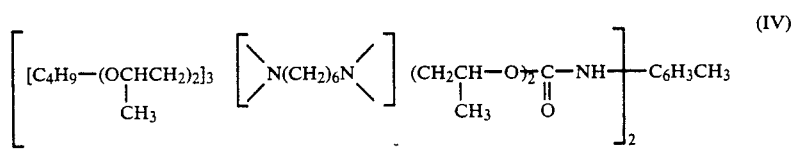

which is the case when the indicated stoechiometric relations are respected, and which may after all easily be eliminated by an additional reaction with a monoalcohol, for example isopropanol.

The product of the invention has excellent neutralizing properties when incorporated into desensitizing inks. It can be used for humid offset, dry offset, typographic or flexographic inks. The new compound can be used in desensitizing inks as a sole compound or as a mixture of two or more representatives.

However, these are only examples, and the man skilled in the art will be aware that mixtures of all starting products may be used or a combination of the final products in order to adapt the active neutralizing compound to the need in practice.

The following examples are given for illustrating purposes only and will not limit the scope of this invention.

PREPARATION OF A COMPOUND OF THE INVENTION

EXAMPLE 1

In a closed vessel equipped with a heating system, a mechanical stirrer, a thermometer and a dropping funnel, 90 parts by weight of a liquid substance having the formula

EXAMPLE 2

90 parts by weight of the product of formula (I) according to Example 1 are dissolved in 67 parts by weight of xylene in the apparatus described in Example 1. The solution is heated to 75° C., and 10 parts by weight of TDI are added dropwise under stirring. The temperature raises to 85° C. at the beginning of the TDI introduction and is maintained at 110° C. by heating. The reaction is finished after 1½ hours. The xylene is eliminated by vacuum distillation at 110° C.

The product obtained as a residue is fully identical to that of Example 1.

EXAMPLE 3

Example 1 is repeated with the exception to use 92 parts by weight of the compound of formula (I) and 8 parts by weight of TDI.

The temperature of the TDI introduction is 80° C., the reaction temperature is 100° C., and the reaction time is 1 hour.

The amounts of reagents used correspond to an equivalent ratio OH/NCO of 1.4 and a molar ratio hydroxyether/TDI of 2.9:1.

The product has the following properties:

Hydroxyl number 21 mg KOH/g; average weight molecular mass $2000\pm100$; average number molecular mass $850\pm50$; nitrogen content $4.9\pm0.1\%$.

EXAMPLE 4

100 parts by weight of a product having the formula

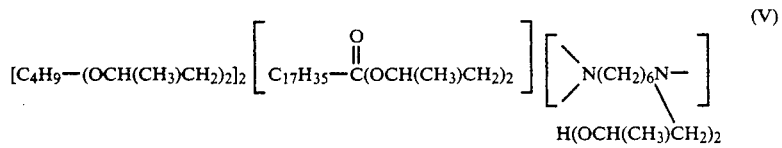

(formula I: $X=>N(CH_2)_6N<$, $R_{1'}=CH_3$, $R_2=C_4H_9$, $R_3=C_{17}H_{35}CO$, $a=4$, $b=2$, $x=2$, $y=1$, $z=0$) are dissolved in 75 parts by weight of xylene in the apparatus described in Example 1. The solution is heated to 70° C., and 8.5 parts by weight of TDI are added dropwise under stirring.

The other operations are identical to those of Example 2.

A slightly yellowish product is obtained having a hydroxyl number of about 20 mg KOH/g and an excellent solubilizing power for oil soluble substances.

The starting product of formula (V) had been obtained by etherification followed by an esterification, using successively butyl bromide and stearoyl chloride in basic medium for the reaction with the tetrafunctional hydroxyl compound of formula (II), wherein $X=>N(CH_2)_6N<$, $R_1$=methyl, $a=4$, $b=2$, without the intermediate isolation of the partial ether.

EXAMPLE 5

The product having the formula

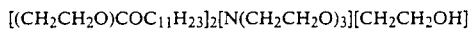

(formula I: $X=N(CH_2CH_2O-)_3-$, residue of triethanolamine; $R_1=H$; $a=3$; $b=1$; $x=z=0$; $R_3=C_{11}H_{23}CO-$; $y=2$), obtained by esterification of the corresponding polyalcohol with lauroyl chloride in basic medium until obtaining an average hydroxyl functionality of the product of about 1, is reacted to form an urethane with hexamethylene diisocyanate in the presence of a tin salt, namely dibutyltin dilaurate. The ratio OH/NCO has been fixed to 1.1, and the reaction is conducted as in Example 1 in the absence of any solvent.

The obtained product is essentially a dimer of the product described above, having in average somewhat less than one urethane group per aminic moiety. The hydroxyl number of the product is about 10 mg KOH/g. It has a clear yellow color. The product has an excellent solubilizing power for oil soluble compounds, and the desensitizing properties of the ink wherein it is incorporated, are excellent.

EXAMPLE 6

The product

(formula II: $X=N(CH_2CH_2O-)_3-$; $R_1=H$; $a=3$; $b=2$; $x=y=z=0$) is mixed with the product

(formula II: $X=(C_2H_5)_2N-$; $R_1=CH_3$; $a=1$; $b=2$; $x=y=z=0$) in a molar ratio of 1:4. The average hydroxyl functionality of the mixture is about 1.4.

The mixture is reacted with toluylene diisocyanate, the ratio OH/NCO being fixed to 1.3, under the same conditions as those described in Example 2, namely in the presence of xylene. The solvent is removed in vacuo, and a very clear product of medium viscosity is obtained, having a hydroxyl number of about 55 mg KOH/g. The product conferes to the ink wherein it is incorporated, excellent neutralizing properties.

PREPARATION AND USE OF AN INK

EXAMPLE 7

An offset desensitizing ink is prepared by thoroughly mixing on a three-roll mill the following substances (the parts are given by weight):

| | |
|---|---|
| product of Example 1 or 2 | 60 parts |
| phenolic resin "Albertol KP 823" | 10 parts |
| titanium dioxide (pigment) | 15 parts |
| calcium carbonate (pigment) | 8 parts |
| propylene glycol (viscosity controller) | 7 parts |

The first two products are mixed together in the warm before incorporating them into the ink.

A comparative offset ink belonging to the state of the art is prepared in the same manner, but the product of Example 1 or 2 is replaced by the same amount of a polypropylene glycol having the same viscosity.

The accepting sheet (CF) of a chemical copying set of paper is printed on certain areas, and the neutralizing power is evaluated by typing crosses with a machine on the upper side of the sheet which carries microcapsules on its back side (CFB).

The amount of printed layer is 2 g/m² and 2.8 g/m² with each one of the two inks.

It is found that the typed crosses are visible even on the desensitized areas when the comparative ink is used, a little bit less clearly where there are 2.8 g/m² of ink, but the crosses are completely invisible on the desensitized areas carrying 2 and 2.8 g/m² of the ink of this invention.

It is therefore possible to reduce the amount of desensitizing ink by surface unit, necessary for desensitizing the receiving sheet in an effective manner, by at least 40%.

The man skilled in the art will easily realize that the compounds of the invention may be incorporated into flexographic and typographic inks. The results of the printing are the same as those described above.

We claim:

1. A desensitizing ink for dry or humid offset, typographic or flexographic printing on a surface of a chemical copying set comprising at least two superimposed sheets whose facing surfaces are covered with an electrophilic layer and a nucleophilic layer, respectively, adapted for a chromogenic reaction upon the application of local pressure, wherein said ink contains an active desensitizing agent comprising at least one nucleophilic compound comprising the addition product of a mono, di or polyisocyanate and an ethoxylated derivative or propoxylated derivative or mixture of ethoxylated and propoxylated derivatives of a primary or secondary mono, di or polyamine or of an alkanolamine, wherein the hydroxyl functionality of the derivative has been reduced after alkoxylation to a value of from 0.5 to 2 by etherification, esterification, or urethanisation.

2. The ink of claim 1 wherein said nucleophilic compound has the formula

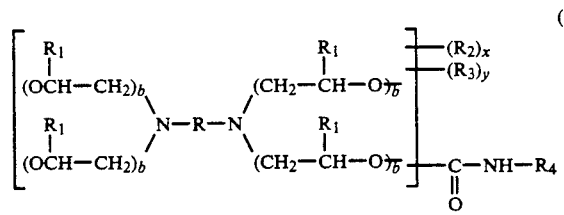
(II)

wherein:
R represents a bivalent aliphatic or bivalent aromatic radical,
$R_1$ is hydrogen or a methyl group,
$R_2$ is an alkyl group,
$R_3$ is the acyl residue of a carboxylic acid having 1 to 22 carbon atoms,
$R_4$ is a substituted or unsubstituted monovalent organic group,
x plus y are equal to about 3, and
b is a number in the range between 1 to 6.

3. The ink of claim 2, wherein R is a radical of the formula —$(CH_2)_i$—wherein i is a number between 2 to 12.

4. The ink of claim 2, wherein R is a bivalent aromatic radical.

5. The ink of claim 2, wherein $R_2$ is a lower alkyl group.

6. The ink of claim 5, wherein $R_2$ is n-butyl.

7. The ink of claim 2, wherein $R_4$ is substituted by at least one substituent of the formula

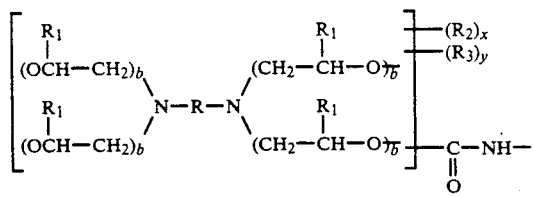

8. The ink of claim 7, wherein said nucleophilic compound has the formula

9. A nucleophilic compound for use as an active agent in a desensitizing ink, comprising the addition product of a mono, di or polyisocyanate and an ethoxylated derivative or propoxylated derivative or mixture of ethoxylated and propoxylated derivatives of a primary or secondary mono, di or polyamine or of an alkanolamine, the hydroxyl functionality of said derivative having been reduced after alkoxylation to a value between 0.5 and 2 by etherification, esterification, or urethanisation.

10. The nucleophilic compound of claim 9, having the formula

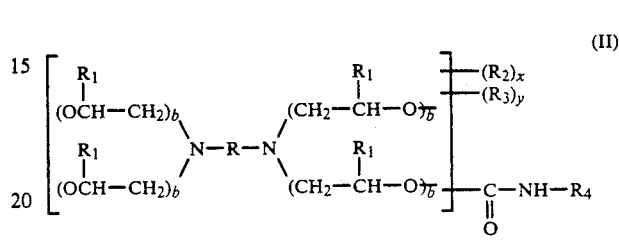
(II)

wherein:
R represents a bivalent aliphatic or bivalent aromatic radical,
$R_1$ is hydrogen or a methyl group,
$R_2$ is an alkyl group,
$R_3$ is the acyl residue of a carboxylic acid having 1 to 22 carbon atoms
$R_4$ is a substituted or unsubstituted monovalent organic group,
x plus y are equal to about 3, and
b is a number in the range between 1 to 6.

11. The nucleophilic compound of claim 10, wherein R is a radical having the formula —$(CH_2)_i$—wherein i is a number between 2 to 12.

12. The nucleophilic compound of claim 10, wherein R is a bivalent aromatic radical.

13. The nucleophilic compound of claim 10, wherein $R_2$ is a lower alkyl group.

14. The nucleophilic compound of claim 13, wherein $R_2$ is n-butyl.

15. The nucleophilic compound of claim 10, wherein $R_4$ is substitued at least one substituent having the formula

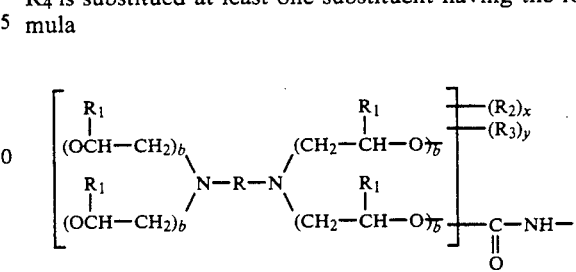

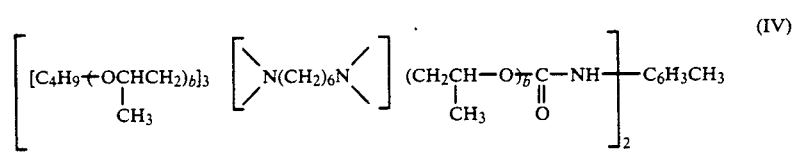
(IV)

wherein b is 2 or 3.

16. The nucleophilic compound of claim 15, having the formula

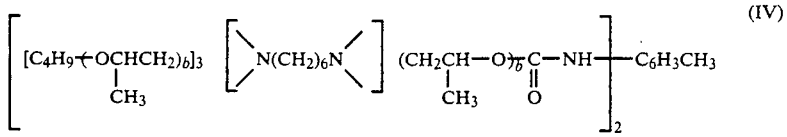
(IV)

wherein b is 2 or 3.

17. A process for the preparation of the compound according to claim 10, comprising the steps of:
   (A) ethoxylating or propoxylating or ethoxylating and propoxylating a primary or secondary mono, di or polyamine, or an alkanolamine;
   (B) reducing the hydroxyl functionality of the product obtained in step (A) to a value between 0.5 and 2 by a reaction selected from the group consisting of etherification, acylating esterification, and urethanisation; and
   (C) reacting the product of step (B) with a mono, di or polyisocyanate.

18. The process of claim 17, wherein a hydroxyether or hydroxyester of formula

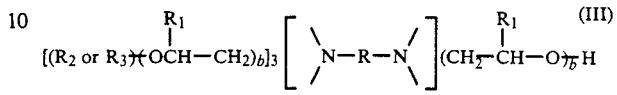
(III)

is reacted with a mono, di or polyisocyanate containing the group $R_4$, wherein R is a bivalent aliphatic or bivalent aromatic radical, $R_1$ is hydrogen or a methyl group, $R_2$ is an alkyl group, $R_3$ is the acyl residue of a carboxylic acid having 1 to 22 carbon atoms and $R_4$ is a substituted or unsubstituted monovalent organic group.

19. The process of claim 18, wherein a diisocyanate of the formula $(OCN)_2R'$ is used, wherein $R'$ is a bivalent aromatic group.

20. The process according to claim 18, wherein a partial ether having the formula

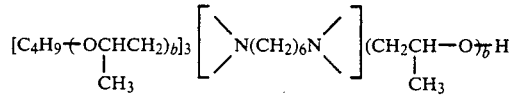

wherein b is 2 or 3, is reacted with toluylene diisocyanate.

* * * * *